United States Patent [19]

Mauskop

[11] Patent Number: 5,538,959
[45] Date of Patent: Jul. 23, 1996

[54] ANALGESIC COMPOSITION FOR TREATMENT OF MIGRAINE HEADACHES

[76] Inventor: Alexander Mauskop, 17A Lafayette Rd., Larchmont, N.Y. 10538

[21] Appl. No.: 378,423

[22] Filed: Jan. 26, 1995

[51] Int. Cl.⁶ .................... A61K 31/615; A61K 31/535
[52] U.S. Cl. ............. 514/165; 514/224.5; 514/300; 514/728; 514/812; 424/44; 424/682; 424/689
[58] Field of Search .............. 424/44, 682, 692; 514/165, 300, 728, 568, 224.5, 812

[56] References Cited

U.S. PATENT DOCUMENTS

| | | | |
|---|---|---|---|
| 3,359,166 | 12/1967 | McClure | 514/365 |
| 3,385,886 | 5/1968 | Nicholson et al. | 562/492 |
| 3,759,980 | 9/1973 | Rosen et al. | 560/143 |
| 3,865,933 | 2/1975 | Mudge | 424/195.1 |
| 4,083,951 | 4/1978 | Goudie et al. | 424/44 |

OTHER PUBLICATIONS

B. M. Altura, "Calcium Antagonist Properties of Magnesium: Implications for Antimigraine Actions", Magnesium 4:169 (1985).

A. Mauskop et al., "Chronic Daily Headache—One Disease or Two? Diagnostic Role of Serum Ionized Magnesium", Cephalalgia 14:24 (1994).

A. Mauskop et al., "Deficiency in Serum Ionized Magnesium but not Total Magnesium in Patients with Migraines. Possible Role of ICa$^{2+}$/IMg$^{2+}$Ratio", Headache 33(3):135 (1993).

F. Facchinetti et al., "Magnesium Prophylaxis of Menstrual Migraine: Effects on Intracellular Magnesium", Headache 31(5):298 (1991).

K. Weaver, "Magnesium and Migraine", Letter to the Editor in Headache 30(2):168 (1990).

*Primary Examiner*—John W. Rollins
*Attorney, Agent, or Firm*—Pennie & Edmonds

[57] ABSTRACT

A magnesium-containing analgesic composition used for treating migraine headaches and methods for using the same are described herein. The composition comprises an analgesic, a magnesium salt and an effervescing agent and is admixed with or dissolved in water prior to ingestion. The symptoms of migraine headache intended to be alleviated include nausea, unilateral pain, dizziness, pulsatile pain, worsening of pain by light physical activity, photophobia and phonophobia.

18 Claims, No Drawings

ANALGESIC COMPOSITION FOR TREATMENT OF MIGRAINE HEADACHES

FIELD OF THE INVENTION

This invention relates to magnesium-based compositions for treating migraine headaches, and methods for using the same.

BACKGROUND OF THE INVENTION

Analgesic compositions comprising magnesium salts have been used to treat a variety of ailments as well as reduce the gastric irritancy often accompanying the oral administration of such analgesic compositions. U.S. Pat. No. 3,865,933 to Mudge teaches the use of a mixture comprising magnesium gluconate, stramonium extract and 3-(2-methylphenoxy)-1,2-propanediol to relieve headache pain. U.S. Pat. No. 3,759,980 to Rosen et al. teaches the use of a mixture of magnesium salicylate and choline salicylate as an analgesic, anti-pyretic, anti-inflammatory and anti-rheumatic agent. U.S. Pat. No. 3,385,886 to Nicholson et al. teaches the use of phenylpropionic acid magnesium salts for the relief of pain, fever and inflammation. U.S. Pat. No. 3,359,166 to McClure teaches the use of magnesium 4-thiazolidinecarboxylate as an analgesic agent. U.S. Pat. No. 4,083,951 to Goudie et al. teaches the use of magnesium acetylsalicylate in conjunction with sodium bicarbonate as an analgesic having reduced gastric irritancy properties. Such compositions have employed magnesium salts for their A deficiency of magnesium, i.e., hypomagnesemia, has been suggested to play a role in migraine headaches (B. A. Altura, *Magnesium*, 4:169 (1985); A. Mauskop et al., *Cephalalgia*, 14:241 (1994)). It had been shown that low serum ionized magnesium ($IMg^{2+}$) levels were found in 42% of patients suffering migraine headaches (A. Mauskop et al., *Headache*, 33(3):135 (1993)). The magnesium salt of pyrrolidone carboxylic acid has been used to treat women with premenstrual migraine headache (F. Facchinetti et al., *Headache*, 31(5):298 (1991)). Amino-chelated magnesium compounds have been used to treat patients with classic migraine headache (K. Weaver in "Letter to the Editor," *Headache*, 30(2):168 (1990)).

When some magnesium-based compositions are administered to patients having migraines, severe headaches or other painful conditions, the slowing of gastric motility which often accompanies these conditions delays the absorption of any medication taken orally. Such a delay in absorption is often more pronounced with tablet than with liquid medicaments. As a result, the onset of action associated with such compositions administered to migraine patients is undesirably delayed, resulting in the prolongation of pain and discomfort to the patient. Thus, there remains a need for compositions which can be used for treating migraine headaches and which are rapidly absorbed and provide rapid onset of action.

SUMMARY OF THE INVENTION

The present invention relates to a method for treatment of migraine headaches which comprises orally administering to a person in need of such treatment a rapidly absorbed magnesium-containing analgesic composition in an amount effective to relieve at least some symptoms of such headaches. Such compositions include various proportions of an analgesic agent, a magnesium salt and an effervescing agent.

Prior to ingestion, such compositions are admixed with or dissolved in water, preferably in about 2–10 ounces of water. Such compositions are ingested as their aqueous admixture or solution, preferably within 1–2 minutes of admixture or dissolution.

DETAILED DESCRIPTION OF THE INVENTION

According to the present invention, improved absorption and hence improved onset of action of a preparation for treating a patient with a migraine headache can be achieved by administering to a patient with a migraine headache a magnesium-containing analgesic composition.

Such analgesic agents which can comprise the magnesium-containing analgesic composition of the present invention include, but are not limited to, acetylsalicylic acid, acetaminophen, paracetamol, ibuprofen, non-steroidal anti-inflammatory drugs, opiates such as codeine and morphine, pharmaceutically acceptable salts thereof, and mixtures thereof. Such pharmaceutically acceptable salts include, but are not limited to hydrochloride, hydrobromide, phosphate, sulfate, acetate, succinate, ascorbate, tartrate, gluconate, benzoate, malate, fumarate, and the like.

The magnesium component of the magnesium-containing analgesic composition of the present invention is ionic magnesium (i.e., $Mg^{2+}$). Suitable sources of $Mg^{2+}$ are magnesium salts which include, but are not limited to magnesium chloride, magnesium citrate, magnesium tartrate, magnesium oxide, magnesium carbonate, magnesium sulfate and the like. Where the analgesic to be included in the magnesium-containing composition is a carboxylic acid, such as for example acetylsalicylic acid, the magnesium salt can be magnesium acetylsalicylate. This is convenient in combining both important components within a single compound. When the magnesium salt of the analgesic is included in the magnesium-containing analgesic composition of the present invention, an additional analgesic may or may not be included.

It is advantageous for the composition to be rapidly absorbed by the subject following oral administration. There are a number of ways to formulate such compositions to achieve rapid absorption, and one of ordinary skill in the art would be aware of such ways. Generally, encapsulating the active ingredient or employing other forms of delaying the release of the agent into the subject should be avoided, except when such means to delay release are included in combination with a rapidly absorbed form of such agent. This could be used, for example, when the composition is intended to provide both a rapidly absorbed initial administration of the analgesic agent, followed by a delayed release of longer duration administered for continued relief of headache symptoms.

In the preferred form of a rapidly absorbable magnesium-containing analgesic composition, an effervescing agent is included. By "effervescing agent" is meant any compound which, upon dissolution in water, provides effervescence to the aqueous mixture or solution upon release of carbon dioxide. Such effervescing agents include, but are not limited to, alkali or alkaline earth metal carbonates or bicarbonates, including, but not limited to sodium carbonate, sodium bicarbonate, sodium glycine carbonate, calcium carbonate and magnesium carbonate. Preferably, the effervescing agent is sodium bicarbonate.

The magnesium-containing analgesic composition may optionally comprise accessory ingredients including, but not limited to dispersing agents such as microcrystalline cellulose, starch, cross-linked poly(vinyl pyrrolidone), and sodium carboxymethyl cellulose; flavoring agents; coloring agents; binders; preservatives; surfactants and the like.

The analgesic agent is advantageously present in the magnesium-containing composition at levels ranging from 10–90 wt. %, preferably 10–75 wt. %.

When added as a separate component, the magnesium salt is present in the magnesium-containing composition at levels ranging from 5–30 wt. %, preferably 10–30 wt. %. When a single compound of a magnesium salt of the analgesic agent is used, the amounts of such a single compound would be between about 20 and 95 wt. % of the composition.

The effervescing agent is present in the magnesium-containing composition at levels ranging from 20–80 wt. %, preferably 25–75 wt. %.

Of course, the total amounts of these components would be 100 wt. %, and those of ordinary skill in the art can vary the amounts within the stated ranges to achieve useful compositions.

The intended route of administration of the magnesium-containing analgesic compositions of the present invention is oral, wherein the composition is admixed with or dissolved in a pre-determined account of water prior to ingestion.

Compositions of the present invention which are suitable for oral administration may be presented as discrete units such as capsules, cachets or tablets, as a powder or granules; as a solution or a suspension in an aqueous liquid or non-aqueous liquid; or an oil-in-water or water-in-oil liquid emulsion. Preferably, the composition of the present invention is presented in tablet form.

Such tablets may be conventionally formed by compression or molding. Compressed tablets may be prepared by compressing in a suitable machine the mixture of one or more analgesic(s), magnesium salt(s), and effervescing agent(s) and optionally one or more accessory ingredients listed above. Molded tablets may be made by molding in a suitable machine the above mixture which can optionally be moistened with an inert liquid diluent. The tablets may optionally be coated or scored, having indicia inscribed thereupon, and may be so formulated as to provide slow or controlled release of the analgesic, magnesium or effervescing compounds therein.

Such tablets can range in weight from 25–2000 mg., preferably from 100–1000 mg., and most preferably from 250–1000 mg.

Prior to ingestion, such compositions are admixed or dissolved in about 2–10 ounces of water, preferably about 4–8 ounces of water. The compositions of the present invention are ingested as their aqueous admixture or solution within 2 minutes, preferably within 1 minute, of their admixture with or dissolution in water, so as to maximize their effervescence and hence absorptive properties.

The compositions are administered shortly after the onset of migraine symptoms. Such symptoms include nausea, unilateral pain, dizziness, pulsatile pain, worsening of pain by light activity, photophobia and phonophobia.

Administration can continue every 2–6 hours, preferably every 4 hours until migraine symptoms have subsided. In patients who suffer from chronic migraine headaches, a daily administration of 1000 mg. of the magnesium-containing composition four times per day of the present invention is advantageous.

EXAMPLE 1

Magnesium-Containing Analgesic Composition A

| Ingredient | mg./Tablet |
| --- | --- |
| Acetylsalicylic Acid | 800 |
| Magnesium Chloride | 250 |
| Sodium Bicarbonate | 500 |
| Poly(ethylene Glycol) 4000 | 50 |

EXAMPLE 2

Magnesium-Containing Analgesic Composition B

| Ingredient | mg./Tablet |
| --- | --- |
| Magnesium Acetylsalicylic Acid | 1000 |
| Sodium Bicarbonate | 350 |
| Citric Acid | 75 |

EXAMPLE 3

Magnesium-Containing Analgesic Composition C

| Ingredient | mg./Tablet |
| --- | --- |
| Acetaminophen Na Salt | 1000 |
| Magnesium Tartrate | 200 |
| Magnesium Carbonate | 200 |

EXAMPLE 4

Magnesium-Containing Analgesic Cocktail

The tablet of Examples 1, 2 or 3 is added to 8 ounces of tap water. The resulting cocktail is ingested within 1 minute of admixture with or dissolution in water.

EXAMPLE 5

Results of Administration of
Magnesium-Containing Analgesic Cocktail to
Patients with Migraine Headaches Methods Five subjects were selected to participate in this study. Included were patients who had daily, but not necessarily continuous migraine headaches. Patients could have had headache-free periods lasting for hours and on a rare occasion for a day. Average severity of headaches prior to and two hours following administration of the magnesium-containing analgesic cocktail described below were assessed on a 1 to 10 verbal scale. Patients taking acetaminophen or non-steroidal anti-inflammatory drugs were excluded from this study.

| Magnesium-Containing Analgesic Cocktail Three tablets each having the following formulation: | |
| --- | --- |
| Ingredient | mg./Tablet |
| Acetylsalicylic acid | 325 |
| Sodium Bicarbonate | 1916 | were dissolved in a solution of 500 mg of magnesium sulfate in 7 ounces of water and administered to each of five patients suffering migraine headache by ingestion of the resulting cocktail within 1 minute of dissolution of each of the three tablets. The results, compiled from a survey of each patient taken 2 hours following ingestion of the cocktail are show below in Table 1:

RESULTS

TABLE 1

| N | Age | Sex | Severity Prior to Administration | Severity Following Administration |
|---|-----|-----|----------------------------------|-----------------------------------|
| 1 | 33  | F   | 10                               | 4                                 |
| 2 | 35  | F   | 7                                | 2                                 |
| 3 | 14  | F   | 8                                | 3                                 |
| 4 | 59  | F   | 7                                | 1                                 |
| 5 | 30  | M   | 8                                | 2                                 |

Thus for all patients included in this study, the administration of the above-described magnesium-containing analgesic composition significantly reduced the severity of migraine headaches.

The magnesium-containing analgesic compositions of the present invention can be used to treat patients with migraine headaches. It is to be understood that such uses are not limited to treating the symptoms of migraine headaches but rather include treating other maladies including non-migraine headache pain, muscular pain, fever associated with viral or bacterial infection, thrombotic diathesis, magnesium deficiency and gastric discomfort.

The present invention is not be limited in scope by the specific embodiments disclosed in these examples which are intended to illustrate the most preferred embodiments of the invention. Indeed, various modifications of the invention or other embodiments which are functionally equivalent to those shown and described herein will become apparent to those skilled in the art and are intended to be covered by the appended claims.

What is claimed:

1. A method for treatment of migraine headaches which comprises orally administering to a person in need of such treatment a rapidly absorbed composition in an amount effective to relieve at least some symptoms of such headaches, said composition consisting essentially of an analgesic agent, a magnesium salt and an effervescing agent.

2. The method of claim 1 wherein the analgesic agent is in the form of a magnesium salt of the analgesic agent.

3. The method of claim 2 wherein the magnesium salt of the analgesic agent is present in an amount of 20–95 wt. % of the composition.

4. The method of claim 2 wherein the analgesic agent is selected from the group consisting of acetylsalicylic acid, acetaminophen, paracetamol, ibuprofen, a non-steroidal anti-inflammatory drug, an opiate or mixtures thereof.

5. The method of claim 1 wherein the analgesic agent is present in an amount of about 10–90 wt. %, the magnesium compound is present in an amount of 5–30 wt. % and the effervescing agent is present in an amount of 20–80 wt. %.

6. The method of claim 1 wherein the analgesic agent is selected from the group consisting of acetylsalicylic acid, acetaminophen, paracetamol, ibuprofen, a non-steroidal anti-inflammatory drug, an opiate, pharmaceutically acceptable salts or mixtures thereof.

7. The method of claim 1 wherein the composition is administered to a person having a deficiency of ionic magnesium.

8. The method of claim 1 wherein the symptoms to be relieved are selected from the group consisting of unilateral pain, nausea, dizziness, pulsatile pain, worsening of pain by light physical activity, photophobia and phonophobia.

9. A method for treatment of migraine headaches which comprises orally administering to a person in need of such treatment a rapidly absorbed composition in an amount effective to relieve at least some symptoms of such headaches, said composition consisting essentially of an analgesic agent and a magnesium salt.

10. The method of claim 9 wherein the analgesic agent is in the form of a magnesium salt of the analgesic agent.

11. The method of claim 10 wherein the magnesium salt of the analgesic agent is present in an amount of 20–95 wt. % of the composition.

12. The method of claim 10 wherein the analgesic agent is selected from the group consisting of acetylsalicylic acid, acetaminophen, paracetamol, ibuprofen, a non-steroidal anti-inflammatory drug, an opiate or mixtures thereof.

13. The method of claim 9 wherein the analgesic agent is present in an amount of about 10–90 wt. % and the magnesium compound is present in an amount of 5–30 wt. %.

14. The method of claim 9 wherein the analgesic agent is selected from the group consisting of acetylsalicylic acid, acetaminophen, paracetamol, ibuprofen, a non-steroidal anti-inflammatory drug, an opiate, pharmaceutically acceptable salts or mixtures thereof.

15. The method of claim 9 wherein the composition is administered to a person having a deficiency of ionic magnesium.

16. The method of claim 9 wherein the symptoms to be relieved are selected from the group consisting of unilateral pain, nausea, dizziness, pulsatile pain, worsening of pain by light physical activity, photophobia and phonophobia.

17. A method for treatment of migraine headaches which comprises orally administering to a person in need of such treatment a rapidly absorbed composition in an amount effective to relieve at least some symptoms of such headaches, said composition consisting essentially of a magnesium salt.

18. The method of claim 17 wherein the symptoms to be relieved are selected from the group consisting of unilateral pain, nausea, dizziness, pulsatile pain, worsening of pain by light physical activity, photophobia and phonophobia.

* * * * *

UNITED STATES PATENT AND TRADEMARK OFFICE
CERTIFICATE OF CORRECTION

PATENT NO. : 5,538,959

DATED : July 23, 1996

INVENTOR(S) : Alexander Mauskop

It is certified that error appears in the above-indentified patent and that said Letters Patent is hereby corrected as shown below:

Column 1, line 31, please delete the incomplete sentence: "Such compositions have employed magnesium salts for their"

Signed and Sealed this

Eighteenth Day of February, 1997

Attest:

BRUCE LEHMAN

*Attesting Officer*  *Commissioner of Patents and Trademarks*